United States Patent [19]
Mansfield et al.

[11] Patent Number: 5,527,672
[45] Date of Patent: Jun. 18, 1996

[54] HYDROPHOBIC COATED MEMBRANES

[75] Inventors: Michael A. Mansfield; Larry Sivik, both of Nashua, N.Y.

[73] Assignee: Millipore Investment Holdings Limited, Wilmington, Del.

[21] Appl. No.: 327,934

[22] Filed: Oct. 24, 1994

Related U.S. Application Data

[63] Continuation-in-part of Ser. No. 21,713, Feb. 24, 1993, abandoned.

[51] Int. Cl.$^6$ ..................................................... C12Q 1/68
[52] U.S. Cl. .......................... 435/6; 435/7.92; 435/7.95; 435/970; 436/518; 436/531; 436/807; 436/810; 427/2.11
[58] Field of Search .................................... 436/518, 531, 436/807, 810; 435/6, 7.92, 7.94, 7.95, 970; 422/56, 57; 427/2.11

[56] References Cited

U.S. PATENT DOCUMENTS

| | | | |
|---|---|---|---|
| 4,803,154 | 2/1989 | Uo et al. | 435/810 X |
| 5,200,312 | 4/1993 | Oprandy | 435/5 |

OTHER PUBLICATIONS

Sanchez et al., "Improving the detection of proteins after transfer to polyvinylidene difluoride membranes", *Electrophoresis*, vol. 13, Nos. 9–10, pp. 715–717 (1992).

Pluskal et al., "Immobilon® PVDF Transfer Membrane: A New Membrane Substrate For Western Blotting of Proteins", vol. 4, No. 3, pp. 272–282 (1986).

*Primary Examiner*—Toni R. Scheiner
*Assistant Examiner*—Susan C. Wolski
*Attorney, Agent, or Firm*—Andrew T. Karnakis; Paul J. Cook

[57] ABSTRACT

A portion of a hydrophobic membrane, having an unknown concentration of a first molecule in a sample bound to its surface, is incubated with a second molecule that selectively binds to the first molecule so as to allow determination of its concentration. The membrane is first coated with the first molecule and then dried to render the uncoated portion nonwettable with water. The labeled second molecule selectively binds to the first molecule in the absence of a blocking agent on the membrane.

13 Claims, No Drawings

HYDROPHOBIC COATED MEMBRANES

This application is a continuation in part of application Ser. No. 08/021,713, filed Feb. 24, 1993, now abandoned.

BACKGROUND OF THE INVENTION

This invention relates to modified hydrophobic membranes having at least a portion of their surface coated with a first molecule bound to a labeled second molecule for the first molecule and to analytical processes utilizing the modified hydrophobic membranes.

Molecules including biomolecules, such as proteins and nucleic acids, are applied to microporous membranes to facilitate detection of specific molecules within complex mixtures. The simplest detection system consists of a first molecule bound to the membrane and a second molecule used for the detection. The first molecule is derived from a sample, adsorbed on the membrane, and then reacted with the second molecule. The second molecules most commonly used for detection of proteins and nucleic acid first molecules are themselves labeled proteins, antibodies, lectins, or nucleic acids such as DNA or RNA. Application of the first molecule to the membrane relies on the membrane's inherent ability to adsorb protein and nucleic acids. To take full advantage of the membrane's adsorption capacity, hydrophilic membranes composed of polymers such as nitrocellulose or nylon are wet in aqueous buffer. Hydrophobic membranes such as those composed of polyvinylidene fluoride (PVDF) are wet first in alcohol, equilibrated in deionized water, and then equilibrated in aqueous buffer as disclosed, for example by Reig et al, "Applied and Theoretical Electrophoresis" 1988, Vol. 1, pgs. 59–60. The first molecule then is applied to the membrane directly or transferred from a gel by passive diffusion or in an electrical field. Although the detection protocol can be initiated immediately using the wet membrane, the membrane is often allowed to dry. The membrane must then be rewet before continuing.

In most cases, the amount of first molecule applied the membrane does not saturate the surface of the membrane. Thus, exposed polymer surface area at and surrounding the point of application provides sites for non-specific binding of the second molecule. To circumvent this problem, the first step in detection protocols involves incubation of the membrane in aqueous buffer containing compounds that block the exposed polymer surface area. Common blocking agents are bovine serum albumin (BSA), non-fat dry milk, gelatin, calf thymus DNA, salmon sperm DNA, and yeast tRNA.

Specific detection of first molecules on microporous membranes requires blocking of exposed binding sites prior to introduction of the second molecule as detectors. If the second molecule binds to exposed binding sites on the membrane, it will be unable to bind to the first molecule. Non-specific binding of the second molecule also causes higher background rendering it difficult to distinguish the signal.

Although efficient blocking of the membrane enhances the signal-to-noise ratio, there are several inherent problems with this step. First, depending on the blocking agent used and the first molecule being detected, the blocking step requires between 1 and 18 hours. Second, attachment of blocking agents to exposed areas of the membrane is not permanent. Proteins and nucleic acids adsorb to membranes through electrostatic, ionic or hydrophobic interactions. Since these interactions are noncovalent, blocking agents may desorb from the membrane after initial binding. Thus, blocking agents are included in vast excess in solutions containing the second molecule detection probes. In a similar fashion, first molecules may desorb from the membrane during incubation. Third, if the blocking agent has a higher affinity for the membrane than the first molecule, the first molecule can be displaced from the membrane, decreasing the signal intensity. Fourth, the blocking agent may non-specifically bind to the first molecule, preventing it from interaction with the second molecule detection probe. Fifth, the second molecule may non-specifically bind to the blocking agent either in solution or on the membrane. Non-specific interaction of the second molecule with the blocking agent is often corrected by the addition of detergents to the second molecule-containing solutions. Detergents, however, enhance the undesirable desorption of the first molecules from the membrane thereby reducing signal intensity. These difficulties require that blocking agents be screened for compatibility with the first and second molecules and that the incubation protocols be optimized to obtain a maximum signal.

Prior to the present invention, it was thought the membrane pore structure must be made accessible to aqueous solutions by a pre-wetting step, such as with methanol followed by exchange with water, so that molecules in aqueous diluent could properly interact with membrane-bound first molecules. This perceived requirement, in turn, promulgated the use of a blocking agent to be applied to the membrane over a suitable period of time followed by one or more suitable molecules the last of which comprises the second molecule which is used for detection. The intimate contact of second molecules with the membrane, in turn, necessitates time consuming washing steps to assure complete removal of unbound second molecules from the membrane surface and from the interior volume of the membrane which can lead to nonspecific signal or background. The time required to effectively wash the membrane extends the required analysis time and also represents a period during which the bound second molecule may desorb from the first molecule, thereby reducing the signal intensity.

Accordingly, it would be desirable to provide a hydrophobic membrane, having bound first molecules, which eliminates the need for a blocking agent and minimizes non-specific adsorption of second molecules utilized for detection. In addition, it would be desirable to provide a hydrophobic membrane having bound first molecules which, in turn, are bound to a labeled second molecule in the absence of a blocking agent. Such membranes would eliminate the need for a blocking agent and therefore would eliminate the need of a membrane wetting step to effect deposition of the blocking agent from aqueous solution.

SUMMARY OF THE INVENTION

The present invention is based upon the discovery that a hydrophobic membrane having first molecules adsorbed thereon can be utilized to interact with labeled second molecules without the use of a blocking agent. A first molecule is bound to the hydrophobic membrane by first wetting the membrane to render it accessible to the diluent containing the first molecule and then contacting the wet membrane with the first molecule under conditions to effect adsorption of the first molecule to the membrane. The membrane then is dried to render the membrane hydrophobic. If the first molecule is sufficiently hydrophilic, it can interact with second molecules in aqueous solutions. Since the unmodified surface of the membrane is hydrophobic, the sample first molecule or second molecules will not interact with the unmodified surface. Hence, specific interactions between the second molecule and adsorbed first molecules are localized to the discrete membrane sites where the adsorbed first molecule is present on the surface. These localized regions are able to interact directly with the aqueous enviroment, and the surrounding unmodified areas, free of first molecules, are unable to interact with the aqueous environment. The need to block these sites on the unmodified portions of the membrane is thus unnecessary. Thus the time needed to apply a blocking agent is eliminated.

In addition since the membrane is hydrophobic when the second molecules are contacted with the membrane and first molecules, the second molecules do not penetrate into the membrane pores. This lack of penetration substantially reduces the necessary wash time needed to remove unbound second molecules from the membrane. For example, the time needed to effect immunodetection with the present invention is at least 50% less than that required with presently available immunodetection processes.

The present invention provides a hydrophobic membrane structure free of a blocking agent on which is adsorbed a first molecule which, in turn, is complexed with a labeled second molecule either directly or indirectly. The membrane structure provides a record of the concentration measurement of the first molecule in a sample.

DESCRIPTION OF SPECIFIC EMBODIMENTS

In accordance with this invention, the surface of a hydrophobic membrane is modified with a first molecule by first rendering the membrane wettable with the diluent for the first molecule. In the case where the diluent is water, the membrane is first rendered water-wettable. The membrane then is contacted with the first molecule in the diluent. The thus-modified membrane then is dried to render the unmodified portion of the membrane surface hydrophobic, i.e., nonwettable with water. The modified membrane then is in condition for use with an aqueous composition which contains the detectable second molecule.

The second molecule is labeled such as with a radioisotope, fluorophore, enzyme, or a chromophone so that it is detectable by conventional means. The second molecule in an aqueous diluent is contacted with the first molecule to form a complex including the detectable label. The second molecule can be complexed directly or indirectly with the first molecule. As an example of indirect complexing, the first molecule can be an antigen which is first contacted with a third molecule, which is a first antibody for the antigen. A second molecule which is a labeled second antibody to the first antibody then is contacted with the complex of the antibody. If desired, intermediate antibodies between the first and second antibodies can be utilized to form a labeled complex. In any event, a blocking agent is not utilized.

Representative suitable hydrophobic membranes include polyvinylidene fluoride, polysulfone, polyethersulfone, polyethylene, polypropylene, polytetrafluoroethylene or the like, preferably polyvinylidene fluoride.

In order to adsorb a first molecule in aqueous diluent to the hydrophobic membrane, the membrane is rendered wettable with water by first immersing the membrane in a water miscible solvent which can fill the pore structure of the membrane and be exchanged with water. Representative suitable solvents include methanol, ethanol. isopropanol, mixtures thereof or the like. The membrane is immersed in the solvent for a suitable time to fill the membrane pore structure such as between about 15 seconds and 1 minute. The wet membrane is then immersed in water to displace the solvent from the pore structure. The water-exchanged wet membrane is then immersed in or contacted for a suitable time with an aqueous composition containing a first molecule to effect adsorption of the first molecule onto the membrane. Generally, immersion in or contact with the aqueous composition containing the first molecule is between about 1 and 120 minutes. Alternatively, a diluent can be utilized which carries the first molecule and also wets the membrane so that the membrane is wet and the first molecule is adsorbed in one step.

After the first molecules have been adsorbed onto the membrane surface, the membrane is dried to remove residual diluent, e.g. water, from the membrane pore structure. The portion of the membrane containing the adsorbed first molecule retains the ability to interact with an aqueous solution while the membrane surface free of adsorbed first molecule is returned to the hydrophobic state by virtue of drying. Because the portion of the membrane surrounding an area with the adsorbed first molecules is hydrophobic, second molecules in aqueous solutions subsequently contacted with the membrane are able only to interact with the portion of the membrane coated with the adsorbed first molecules.

The membranes of this invention are the result of highly selective binding of the second labeled molecules to the first molecules. The absence of a blocking agent prevents desorption of first molecules which would normally desorb during incubation of the membrane in the diluent containing the blocking agent. Furthermore, nonspecific binding of a blocking agent to the first molecule or of the second molecule to a blocking agent is eliminated. Thus, the membranes of this invention, comprising a hydrophobic membrane to which is adsorbed a complex of a first molecule and a labeled second molecules provide a more accurate measure of the first molecule in a sample.

The first molecule can be any molecule which has a complementary second molecule with which it can interact to form a complex molecule. Representative suitable first molecules include proteins, antigens, antibodies, lectins, nucleotides, glycoproteins, amino acids, nucleic acids such as peptide nucleic acid, DNA, RNA or the like. The particular first molecule used is dependent upon the particular second molecule available for detection. The first and second molecules are complementary in that they form a complex together selectively. The second molecule does not interact with portions of the membrane which are hydrophobic and which are free of first molecules. The second molecule can be labeled with a radioactive label, a fluorescent label, an enzyme or any other moiety that reacts with a reagent so that it can be detected or itself can be the detected reagent. Alternatively, the first molecules can be complexed with a molecule such as any enzyme that can be activated to render it detectable prior to adsorbing the first molecule on the membrane. The complex molecule immobilized on the membrane then can be detected directly by analyzing for the label on the second molecule or indirectly using a detection reagent. Representative suitable labels include $^{125}I$, $^{99m}Tc$, $^{35}S$, $^{32}P$, colloidal gold, colloidal iron, fluoroscein or the like. Additional suitable labels include alkaline phosphatase, horseradish peroxidase, streptavidin or the like. The second molecules are in aqueous solution, preferably water or phosphate buffered saline (PBS) during interaction with the immobilized first molecule.

The following examples illustrate the present invention and are not intended to limit the same.

EXAMPLE I

A 0.45 micron microporous polyvinylidene fluoride membrane was immersed in 100% methanol solution for 5 seconds at room temperature to render the surface hydrophilic. The membrane was transferred to deionized water for 2 minutes to displace the methanol and then equilibrated in a solution of 25 mM Tris, 192 mM glycine, 10% methanol for 15 minutes. The membrane was then placed in contact with a polyacrylamide gel on which the protein transferrin was previously resolved by electrophoresis. The membrane/gel assembly was placed in a reservoir of 25 mM Tris, 192 mM glycine, 10% methanol, and the transferrin was transferred from the gel to the membrane using an electrical field oriented perpendicular to the plane of the gel and membrane. After transferring the protein for 2 hours at a field strength of 8 volts per cm intra-electrode distance, the membrane was removed and dried at room temperature for 2 hours to make the uncoated portions of the membrane hydrophobic.

The membrane was then contacted with an aqueous solution containing the antibody goat [anti-transferrin] IgG for 1 hour at room temperature. Following two rinses of 15 seconds in aqueous buffer, the membrane was contacted for 30 min at room temperature with an aqueous solution containing rabbit [anti-(goat IgG)] IgG which was conjugated to alkaline phosphatase. Following two rinses of 15 seconds in aqueous buffer, the membrane was placed in contact with an aqueous solution containing 3-bromo-4-chloro-5-indolyl phosphate and nitroblue tetrazolium. After allowing 10 minutes for color development, the membrane was rinsed in water and dried at room temperature.

The results were as follows:

1) During the antibody incubations and rinses, the membrane did not visibly wet.

2) Transferrin was detected as a single band in each sample.

3) As little as 1 picogram of transferrin was detected. Omission of the blocking step and reduction of the rinse times between probe solutions and visualization solution did not reduce sensitivity.

4) Based on the lack of background, the antibody probes did not bind to the hydrophobic areas of the membrane.

EXAMPLE II

A membrane coated with first protein was prepared as described in Example I except that the polyacrylamide gel contained a dilution series of human serum prepared from whole blood. The serum samples contained a complex pattern of proteins; transferrin was one of these proteins. Transferrin was detected in these samples as described in Example I.

The results are as follows:

1) During the antibody incubations and rinses, the membrane did not visibly wet.

2) Transferrin was detected as a single band in each sample. Omission of the blocking step and reduction of the wash times between probe solutions and visualization solution did not cause non-specific reaction of the antibody with other proteins.

3) Transferrin was detected at a dilution of 1:327,680. Omission of the blocking step and reduction of the rinse times between probe solutions and visualization solution did not reduce sensitivity.

4) The specificity of the antibodies was not altered. Other serum proteins did not react with the antibody probes.

5) Based on the lack of background, the antibody probes did not bind to the hydrophobic areas of the membrane.

EXAMPLE III

A 0.45 micron microporous polyvinylidene fluoride membrane was immersed in 100% methanol solution for 5 seconds at room temperature to render the surface hydrophilic. The membrane was transferred to deionized water for 2 minutes to displace the methanol and then equilibrated in a solution of 25 mM Tris, pH 10.4, 10% methanol for 15 minutes. The membrane was then placed in contact with a polyacrylamide gel on which the glycoproteins transferrin, a 1-acid glycoprotein, and ribonuclease B had been previously resolved by electrophoresis. The membrane/gel assembly was sandwiched between filter paper soaked in 25 mM Tris, 10% methanol, pH 10.4 and filter paper soaked in 25 mM Tris, 40 mM glycine, 10% methanol, pH 9.4. The proteins were transferred from the gel to the membrane using an electrical field oriented perpendicular to the plane of the gel and membrane. After transferring the protein for 45 minutes at a field strength of 1.5 milliamps per $cm^2$ of gel surface area, the membrane was removed and dried at room temperature for 2 hours to make the uncoated portions of the membrane hydrophobic.

The membrane was then cut into strips; and individual strips were contacted for 1 hour at room temperature with an aqueous solution containing one of the following biotinylated lectins; wheat germ agglutinin, ricin, or Datura stramonium agglutinin. Following two rinses of 15 seconds in aqueous buffer, the membrane strips were contacted for 30 min at room temperature with an aqueous solution containing a complex between avidin and biotinylated alkaline phosphatase. Following two rinses of 15 seconds in aqueous buffer, the membrane strips were contacted for 30 min at room temperature with an aqueous solution containing 3-bromo-4-chloro-5-indolyl phosphate and nitroblue tetrazolium. After allowing 1–2 minutes for color development, the membrane strips were rinsed in water and dried at room temperature.

The results were as follows:

1) During the lectin incubations, the membrane did not visibly wet.

2) Ricin bound to transferrin and a 1-acid glycoprotein, while wheat germ agglutinin and Datura stramonium agglutinin bound primarily to a 1-acid glycoprotein. No reaction of these lectins with ribonuclease B was observed.

3) Omission of the blocking step and reduction of the rinse times between probe solutions and visualization solution did not reduce sensitivity.

4) Based on the lack of background, the probe complex did not bind to hydrophobic areas of the membrane.

5) Specific detection of the protein bands indicated that a complex composed of two non-covalently associated molecules can bind to proteins bound to a hydrophobic membrane.

EXAMPLE IV

Human serum (Sigma) and goat anti-(human transferrin) (Sigma) were stored in aliquots at −70°. Alkaline phosphatase and horseradish peroxidase conjugates of rabbit anti-(goat lgG) and corresponding enzyme substrates were obtained from Kirkegaard and Perry Laboratories and stored at 4°. All other chemicals were reagent grade and prepared in Milli-$Q^R$ water.

Human serum was serially diluted in electrophore ample buffer (0.112 M tris acetate, pH 7, 2% (w/v) bromophenol blue), and 5-ul aliquots were loaded onto precast, 10-20% polyacrylamide gradient mini-gels (Millipore). The proteins were resolved at 200 V for 30–35 min. Proteins were then transferred from the gel to a polyvinylidene fluoride (PVDF)

membrane (Immobilon-P) by tank transfer in 25 mM Tris, 192 mM glycine, 10% (v/v) methanol, for 2 hours at 7 V/cm inter-electrode distance or by semi-dry transfer for 45 min at 1.5 mA/cm$^2$ on a MilliBlot Graphite Electroblotter using a three buffer system. After transfer, the blots were allowed to dry completely.

The general incubation schemes for immunodetection on standard and hydrophobic blots are shown in Table 1. Blocking buffer consisted of 1% BSA in PBS (phosphate-buffered saline: 10 mM Na-phosphate, pH 7.2, 0.9% NaCl). Primary and secondary antibodies were diluted 1:1000 and 1:2000, respectively, in 1% BSA, 0.05% Tween-20, in PBS, and used at a ratio of 0.09 ml/cm$^2$ of membrane surface area. Disposable polystyrene weigh boats used for incubations gave good mixing when agitated and permitted easy handling of the blots. Blots were washed in plastic containers using PBS at a ratio of 0.9 ml/cm$^2$ of membrane surface area. For visualization, the blots were laid out on a piece of Saran wrap. The substrate solutions, prepared immediately before use, were applied with a pipet (0.045 ml/cm$^2$). Blots visualized with 5-bromo-4-chloro-3-indolyl phosphate/nitroblue tetrazolium (BCIP/NBT) were incubated for 10 min and those visualized with 4-chloro-1-naphthol (4CN) for 20 min. To stop the reaction, the blots were rinsed in Milli-Q water. The blots were imaged on a Bio Image® Electrophoresis Analyzer.

TABLE 1

Immunodetection Incubation Schemes for Standard and Hydrophobic Blots

| Step | Standard Blot | Hydrophobic Blot |
| --- | --- | --- |
| 1. Wet in methanol and water exchange | 5 min | None |
| 2. Block[1] | 1 hour | None |
| 3. Primary antibody | 1 hour | 1 hour |
| 4. Wash | 3 × 10 min | 2 × 10 sec |
| 5. Secondary antibody | 1 hour | 30 min |
| 6. Wash | 3 × 10 min | 2 × 10 sec |
| 7. Substrate (BCIP)[2] | 10 min | 10 min |
| 8. Total time[2] | 4 hour 15 min | 1 hour 41 min |

[1]Buffer compositions are described above.
[2]Add 10 min for incubation with 4CN.

To show the entire spectrum of proteins bound to the membrane, the blot was stained with Coomassie blue. Two lanes contain serum diluted 1:320 to show those proteins that are not present in high enough concentration to be visible in the other lanes. Sample dilutions and estimated transferrin content (based on a serum concentration of 0.4 mg/ml) are as follows:

| | Dilution | ng transferrin |
| --- | --- | --- |
| Lane 1 | 1:1280 | 1.56 |
| Lane 2 | 1:2560 | 0.78 |
| Lane 3 | 1:5120 | 0.39 |
| Lane 4 | 1:10240 | 0.19 |
| Lane 5 | 1:20480 | 0.097 |
| Lane 6 | 1:40960 | 0.049 |
| Lane 7 | 1:81920 | 0.024 |
| Lane 8 | 1:163840 | 0.012 |
| Lane 9 | 1:327680 | 0.006 |
| Lane 10 | 1:655360 | 0.003 |

Blots were prepared by tank transfer as described above. They were processed for immunodetection as described in Table 1 using an alkaline phosphatase-conjugated secondary antibody and BCIP/NBT as the substrate for visualization. The maximum sensitivity achieved on the standard blot was 1:81920; while the maximum sensitivity achieved on the hydrophobic blot was 1:163840.

Blots were prepared by tank transfer as described above. They were processed for immunodetection as described in Table 1 using a horseradish peroxidase-conjugated secondary antibody and 4CN as the substrate for visualization. The maximum sensitivity achieved on the standard blot was 1:20480; while the maximum sensitivity achieved on the hydrophobic blot was 1:5120.

Blots were prepared by tank transfer as described above. They were processed for immunodetection as described in Table 1 except that 1% non-fat milk was used as a blocking agent instead of 1% BSA in the blocking and antibody buffer solutions. An alkaline phosphatase-conjugated secondary antibody and BCIP/NBT were used for visualization. The maximum sensitivity achieved on the standard blot was 1:20480; while the maximum sensitivity achieved on hydrophobic blot was 1:5120.

Blots were prepared by semi-dry transfer as described above. They were processed for immunodetection as described in Table 1 using an alkaline phosphatase-conjugated secondary antibody and BCIP/NBT as the substrate for visualization. The maximum sensitivity achieved on both blots was 1:40960.

Immobilon-P, which is composed of PVDF, is inherently hydrophobic; and aqueous buffers can not penetrate the pore structure. The data presented here clearly demonstrate that the wetting step is not required for immunodetection of transferrin. The hydrophobic blot procedure is compatible with blots prepared by both tank and semi-dry transfer and with the substrates BCIP and 4CN. Additionally, the binding specificity of anti-transferrin is not altered by the hydrophobic blot protocol described in Table 1.

There are several advantages to the hydrophobic blot procedure of this invention. First, the blocking step can be omitted without resulting in substantially different backgrounds between hydrophobic blots and standard blots. Second, the wash steps can be reduced dramatically, in this case to a total of 20 seconds. Because the pore structure is inaccessible to the buffers, antibodies are restricted to the outer surface of the membrane. Removal of unbound antibodies is simply a matter of washing excess buffer from the surface. For standard blots, the washes are considerably longer to allow time for fluid exchange in and out of the pores. Third, the total time required to complete immunodetection on a hydrophobic blot is less than half that required for standard immunodetection.

EXAMPLE V

A membrane with adsorbed protein was prepared as described in Example II except that the membrane was composed of polypropylene. Transferrin was detected on this membrane as described in Example I.

The results are as follows:

1) During antibody incubation and rinses, the membrane did not visibly wet.

2) Transferrin was detected as a single band in each sample. Omission of the blocking step and reduction of the wash times between probe solutions and visualization solution did not cause non-specific reaction of the antibody with other proteins.

3) Transferrin was detected at a dilution of 1:20480. Omission of the blocking step and reduction of the rinse times between probe solutions and visualization did not reduce sensitivity.

4) The specificity of the antibodies was not altered. Other serum proteins did not react with the antibody probes.

5) Based on the lack of background, the antibody probes did not adsorb to the hydrophobic areas of the membrane.

EXAMPLE VI

A membrane with adsorbed protein was prepared as described in Example II except that the membrane was composed of teflon. Transferrin was detected on this membrane as described in Example I.

1) During antibody incubation and rinses, the membrane did not visibly wet.

2) Transferrin was detected on the membrane at a sample dilution of 1:5120.

3) Based on the lack of background, the antibody probes did not adsorb to the hydrophobic areas of the membrane.

We claim:

1. A process for detecting a first molecule in an aqueous diluent which comprises the following steps in sequence:
   a rendering a surface of a hydrophobic membrane wettable with a water miscible solvent which can fill the pore structure of the membrane and be exchanged with water, and adsorbing said first molecule on discrete areas of said surface,
   b. drying said membrane to render second areas of said membrane surrounding said discrete areas nonwettable with water,
   c. contacting said first molecule with a detectable second molecule in aqueous diluent, wherein said second molecule binds selectively to said first molecule and not with said nonwettable discrete areas of said membrane absence oil, and wherein said membrane is free of blocking agent on said and
   d. detecting said first molecule bound to said second molecule by detecting said second molecule.

2. The proess of claim 1 wherein said first molecule is an antigen.

3. The process of claim 1 wherein said first molecule is an antibody.

4. The process of claim 1 wherein said first molecule is a nucleic acid.

5. The process of claim 1 wherein said first molecule is a glycoprotein.

6. The process of claim 1 wherein said first molecule is a peptide nucleic acid.

7. The process of claim 1 wherein said first molecule is a ribonucleic acid.

8. The process of claim 1 wherein said first molecule is deoxyribonucleic acid.

9. The process of claim 1 wherein rendering said surface wettable and adsorbing said first molecule are conducted in one step.

10. The process of claim 1 wherein rendering said surface wettable and adsorbing said first molecule are conducted sequentially.

11. The process of claim 1 wherein said first molecule is first contacted with a third molecule which binds selectively to said first molecule and wherein said second molecule binds selectively, to said third molecule and thereby is bound selectively to said first molecule through said third molecule.

12. The process of claim 11 wherein said first molecule is deoxyribonucleic acid.

13. The process of claim 11 wherein said first molecule of unknown concentration is a ribonucleic acid.

* * * * *